United States Patent [19]
Snyder et al.

[11] Patent Number: 5,525,329
[45] Date of Patent: Jun. 11, 1996

[54] INHIBITION OF PHOSPHODIESTERASE IN OLFACTORY MUCOSA

[75] Inventors: Solomon H. Snyder; Gabriele V. Ronnett, both of Baltimore, Md.; Anne M. Cunningham, Annandale, Australia; Craig B. Warren, Rumson, N.J.; Felice F. Borisy, Baltimore, Md.

[73] Assignee: The Johns Hopkins University, Baltimore, Md.

[21] Appl. No.: 367,765

[22] Filed: Jan. 3, 1995

Related U.S. Application Data

[63] Continuation of Ser. No. 886,258, May 21, 1992, abandoned.

[51] Int. Cl.$^6$ .............................. A61K 31/52; A61K 9/12
[52] U.S. Cl. .............................. 424/45; 424/43; 514/263; 514/937; 514/957
[58] Field of Search .............................. 424/43, 45, 434; 514/263, 183, 957, 937

[56] References Cited

PUBLICATIONS

Borisy, et al., "Calcium/Calmodulin–activated Phosphodiesterase Expressed in Olfactory Receptor Neurons", *J. of Neuroscience*, 12(3):915–923 (Mar. 1992).

Broughton, et al., "New Inhibitor of Reagin–mediated Anaphylaxis", *Nature*, 251:650–652 (Oct. 18, 1974).

Hidaka, et al., "Selective Inhibitors of Three Forms of Cyclic Nucleotide Phosphodiesterase—Basic and Potential Clinical Application", *Advances in Cyclic Nucleotide and Protein Phosphorylation Research*, vol. 16, edited by S. J. Strada and W. J. Thompson, Raven Press, New York © 1984.

Kramer, et al., "Selective Inhibition of Cyclic Nucleotide Phosphodiesterases by Analogues of 1–Methyl–3–Isobutylxanthine", *Biochemistry*, 16(15):3316–3321 (1977).

Ruckstuhl, et al., "Inhibition of Lung Cyclic AMP–and Cyclic GMP–Phosphodiesterases by Flavonoids and Other Chromone–Like Compounds", *Biochemical Pharmacology*, 30(7):697–702, 1981 (printed in Great Britain).

Wells, et al., "Methylxanthine Inhibitors of Phosphodiesterases", *Methods in Enzymology*, 159:489–496, edited by Jackie D. Corbin and Roger A. Johnson, Academic Press, Inc. © 1988.

Menevse, et al., "Evidence for the Specific Involvement of Cyclic AMP in the Olfactory Transduction Mechanism", *Biochemical and Biophysical Research Communications*, 77(2):671–677, 1977.

Vatolkina, et al., "The search for Cyclo–AMP Phosphodiesterase Inhibitors Using Substructural and Topological Descriptors", *Institute of Chemical Physics, Academy of Sciences of the USSR, Moscow*, Received Dec. 5, 1989.

Bowers, et al., "Reassessment of Temporal and Aerodynamic Factors of Olfactory Stimulation in Relation to a Lower Threshold", *J. Physiol. Paris*, 64:303–310, 1972 (w/English Translation).

Savvateeva, et al., "Behavioral Effects of Temperature Sensitive Mutations Affecting Metabolism of cAMP in *Drosophila Melanogaster*", *Pharmacology Biochemistry & Behavior*, 14:603–611, 1981.

Wang, et al., "Calmodulin–Stimulated Cyclic Nucleotide Phosphodiesterases", *Cyclic Nucleotide Phosphodiesterases: Structure, Regulation and Drug Action*, pp. 19–59, edited by J. Beavo and M. Houslay, John Wiley & Sons © 1990.

(List continued on next page.)

Primary Examiner—Thurman K. Page
Assistant Examiner—Raj Bawa
Attorney, Agent, or Firm—Banner & Allegretti

[57] ABSTRACT

The present invention provides the art with methods for enhancing the sense of smell. The method involves application of an inhibitor of phosphodiesterase to the olfactory epithelium. New inhibitors can be screened using one or more phosphodiesterases isolated from olfactory mucosa. Nebulizers for applying inhibitors to the olfactory mucosa are also provided.

10 Claims, 13 Drawing Sheets

OTHER PUBLICATIONS

Conti, et al., "Structure and Function of the Rolipram–Sensitive, Low–$K_m$ Cyclic AMP Phosphodiesterases: A Family of Highly Related Enzymes", *Cyclic Nucleotide Phosphodiesterases: Structure, Regulation and Drug Action,* pp. 243–265, edited by J. Beavo and M. Houslay, John Wiley & Sons © 1990.

Charbonneau, "Structure–Function Relationships Among Cyclic Nucleotide Phosphodiesterases", *Cyclic Nucleotide Phosphodiesterases: Structure, Regulation and Drug Action,* pp. 299–315, edited by J. Beavo and M. Houslay, John Wiley & Sons © 1990.

Erhardt, "Second generation Phosphodiesterase Inhibitors: Structure–Activity Relationships and Receptor Models", *Cyclic Nucleotide Phosphodiesterases: Structure, Regulation and Drug Action,* pp. 317–332, edited by J. Beavo and M. Houslay, John Wiley & Sons © 1990.

Newton, et al., "Cyclic CMP–Specific Phosphodiesterase Activity", *Cyclic Nucleotide Phosphodiesterases: Structure, Regulation and Drug Action,* pp. 141–159, edited by J. Beavo and M. Houslay, John Wiley & Sons © 1990.

Frings, et al. "Current Recording from Sensory Cilia of Olfactory Receptor Cells *In Situ*", *J. Gen. Physiol.,* (Jan. 1991), 97(1) 1–16, (Abstract).

Anholt, et al., "Olfactory transduction: Cross–talk Between Second–Messenger System", *Biochemistry,* (1990), 29(17):4049–54 (Abstract).

Frings, S. et al. (1991 Jan.) J. Gen. Physiol. 97(1):1–16. (Abstract).

Anholt, Robert R. H., et al. (1990). Biochemistry 29(17):4049–54. (Abstract).

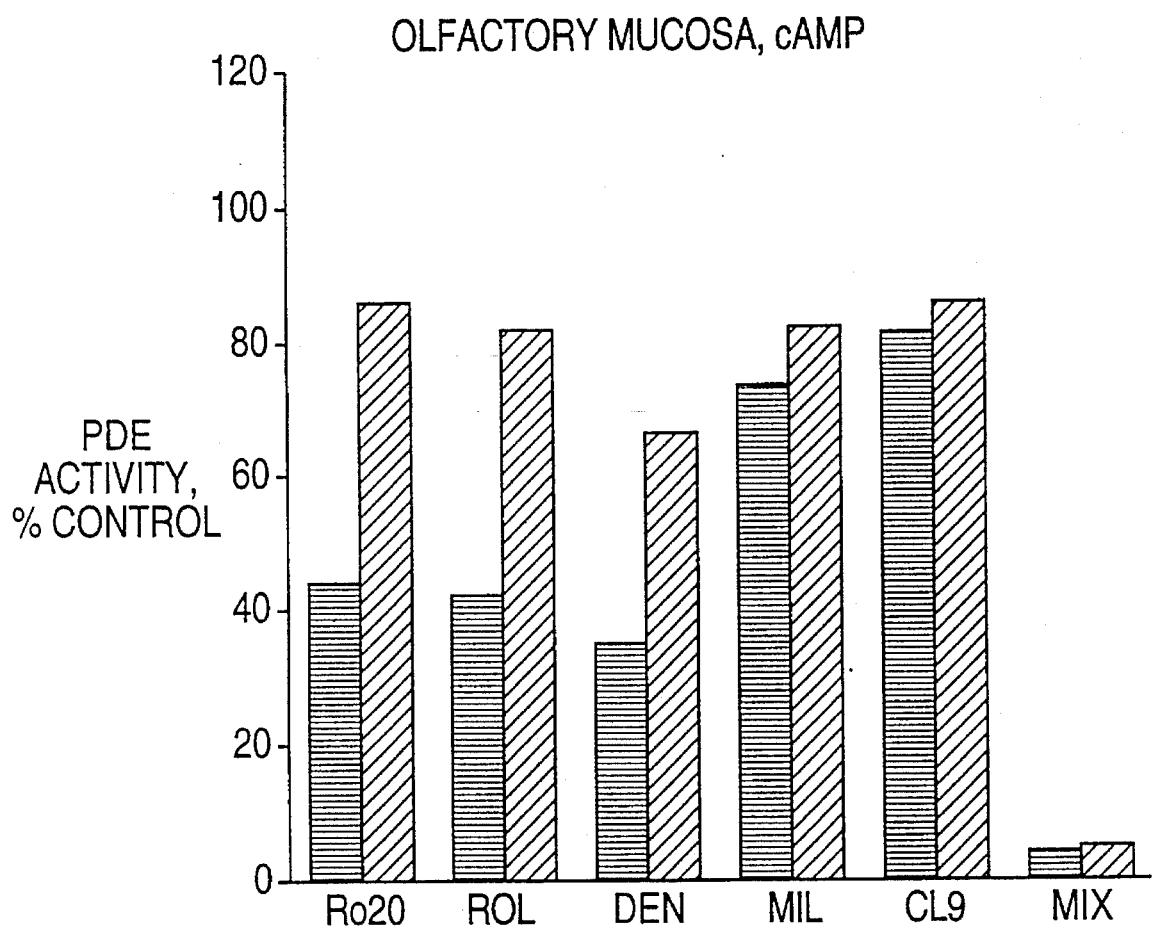

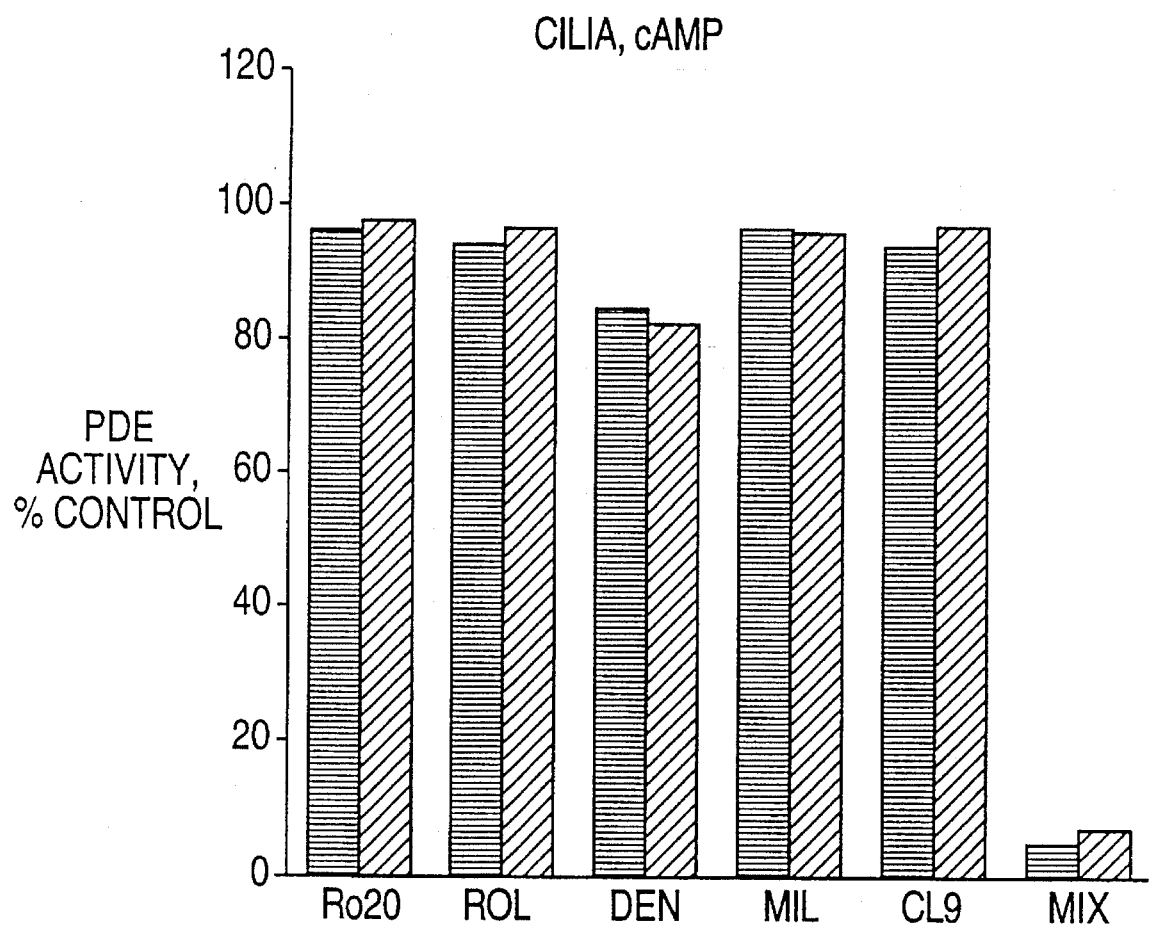

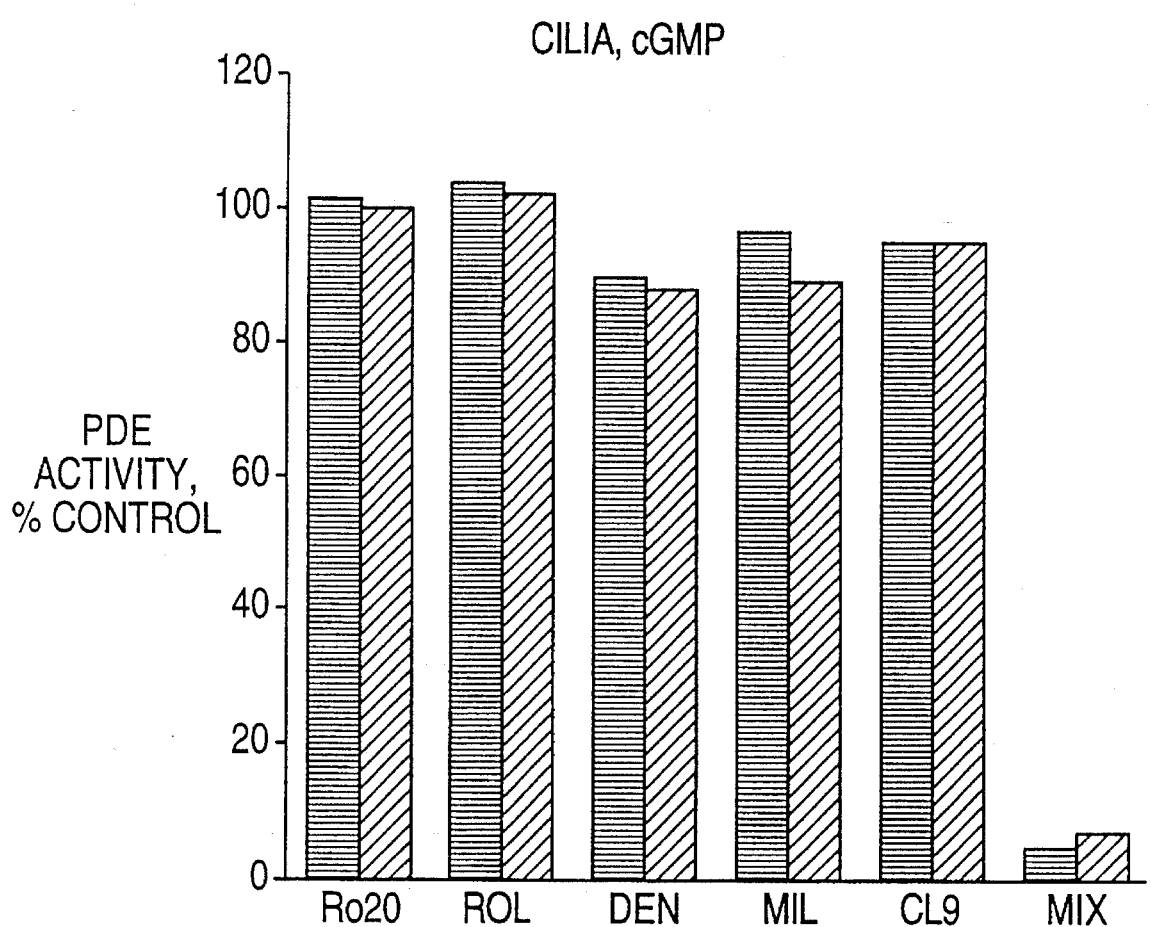

INHIBITION OF PHOSPHODIESTERASE IN OLFACTORY MUCOSA

This invention was made with government support under United States Public Health Service Grant DA-00266 and United States Public Service Research Scientist Award DA-00074. The government has certain rights in this invention.

This application is a continuation of application Ser. No. 07/886,258, filed May 21, 1992, now abandoned.

TECHNICAL FIELD OF THE INVENTION

This application relates to the field of olfactory enhancement. More particularly it relates to the use of an inhibitor of phosphodiesterase found in olfactory mucosa.

BACKGROUND OF THE INVENTION

Olfaction, the sense of smell, begins in the ciliary processes of olfactory receptor neurons. These odorant sensitive neurons are asymmetric bipolar cells situated in a pseudostriatified epithelium, resting on a basal layer of proliferative stem cells and supported apically by sustentacular cells. Each neuron sends a long axon inward through the cribiform plate to synapse in the olfactory bulb, and a dendrite outward into the mucosal layer. The dendrite terminates in a knob from which sprout a number of cilia, wherein occurs olfactory signal transduction.

Cyclic nucleotides, especially cAMP, appear to play a crucial role in olfactory signal transduction. Odorants stimulate adenylyl cyclase activity of olfactory cilia (Pace, et al. (1985) *Nature*, 316:255–258; Sklar, et al. (1986) *J. Biol. Chem.*, 261:15538–15543; Breer, et al. (1990) *Nature* 345:65–68) and primary cultures of olfactory neurons (Ronnett, et al. (1991) *J. Neurosci.*, 11:1243–1255; Ronnett, et al. (1991) *Proc. Natl. Acad. Sci. USA*, 88:2366–2369), effects which can occur extremely rapidly and at very low concentrations of odorants (Boekhoff, et al. (1990) *EMBO Journal*, 9:2453–2458; Ronnett, et al. (1991) *Proc. Natl. Acad. Sci. USA*, 88:2366–2369). The rapid decline in cAMP levels suggests an important regulatory role for phosphodiesterase (PDE).

Several types of PDE have been differentiated, based on their affinities for cyclic nucleotides, activation or inhibition by cGMP, and regulation by $Ca^{2+}$/calmodulin (Thompson, et al. (1972) *Meth. Enzymol.*, 34:205–212; Kincaid, et al. (1988) *Meth. Enzymol.*, 159:457–470; Beavo, J.A. (1988) *Advances in Second Messenger and Phosphoprotein Research.*, 22:1–38). A $Ca^{2+}$/calmodulin PDE (CAM-PDE) activity might be relevant to olfaction, since there is evidence of a role for $Ca^{2+}$ in olfaction. For instance, odorants stimulate the influx of $Ca^{2+}$ into olfactory neurons (Restrepo, et al. (1990) *Science* 249:1166–1168), calmodulin antagonists alter the electro-olfactogram (Winegar, et al. (1988) *Biochem. Physiol.* 91A:309–315) and odorants potently stimulate inositol 1,4,5-trisphosphate ($IP_3$) formation which is associated with the release of sequestered $Ca^{2+}$ (Boekhoff, et al. (1990) *EMBO Journal*, 9:2453–2458; Wood, et al. (1990) *Chem. Senses*, 15:655). Moreover, the adenylyl cyclase whose activity is enhanced by odorants in primary olfactory neuronal cultures, is absolutely dependent upon $Ca^{2+}$ (Ronnett, et al. (1991) *Proc. Natl. Acad. Sci. USA*, 88:2366–2369). There is a need in the art to determine if a PDE plays a role in olfaction, and if it does, to determine what properties this PDE displays.

SUMMARY OF THE INVENTION

It is an object of the invention to provide a method for enhancing the sense of smell in a human.

It is another object of the invention to provide a method for screening compounds for those which enhance the sense of smell.

It is yet another object of the the invention to provide a device for enhancing the sense of smell.

These and other objects of the invention are provided by one or more of the following embodiments. In one embodiment, a method for enhancing the sense of smell in a human is provided. The method comprises:

applying a phosphodiesterase inhibitor to nasal epithelium in an amount sufficient to inhibit phosphodiesterase.

In another embodiment of the invention a method for screening compounds for those which enhance the sense of smell is provided. The method comprises:

contacting a test compound with a phosphodiesterase derived from olfactory neurons;

determining the activity of the phosphodiesterase which has been contacted with the test compound; and comparing the activity of the phosphodiesterase in the presence of the test compound to activity of the phosphodiesterase in the absence of the test compound, a smell enhancer being a test compound which diminishes the activity of the phosphodiesterase.

In yet another embodiment of the invention a device for enhancing the sense of smell is provided. The device comprises:

a nasal nebulizer containing a phosphodiesterase inhibitor, said inhibitor having inhibitory activity toward phosphodiesterase derived from olfactory neurons, said nebulizer capable of aerosolizing said inhibitor.

BRIEF DESCRIPTION OF THE DRAWINGS

FIG. 1 shows the effect of selective pharmacological agents on phosphodiesterase of olfactory turbinates and cilia. PDE activity in homogenates of olfactory turbinates was assayed using 1 μM cAMP or 1 μM cGMP as substrate. Assays were performed with 100 μM $Ca^{2+}$ (hatched bars) or with 100 μM EGTA (solid bars). Abbrev.: Ro20, Ro20-1724; rol, rolipram; den, denbufylline; mil, milrinone; CL 9, CL-930; MIX, 1-methyl-3-isobutyl xanthine. FIG. 1A shows Olfactory mucosa, cAMP PDE activity, assayed at 1 μM cAMP. FIG. 1C is a graph showing Olfactory cilia, cAMP PDE activity, assayed at 1 μM cAMP. FIG. 1D shows Olfactory cilia, cGMP PDE activity, assayed at 1 μM cGMP.

FIG. 3 compares phosphodiesterase activities in olfactory cilia and homogenates of olfactory epithelium, respiratory epithelium, and cerebral cortex.

FIG. 4 shows phosphoditesrase activity in cilia as a function of calmodulin concentration.

DETAILED DESCRIPTION OF THE INVENTION

Figure 1B:
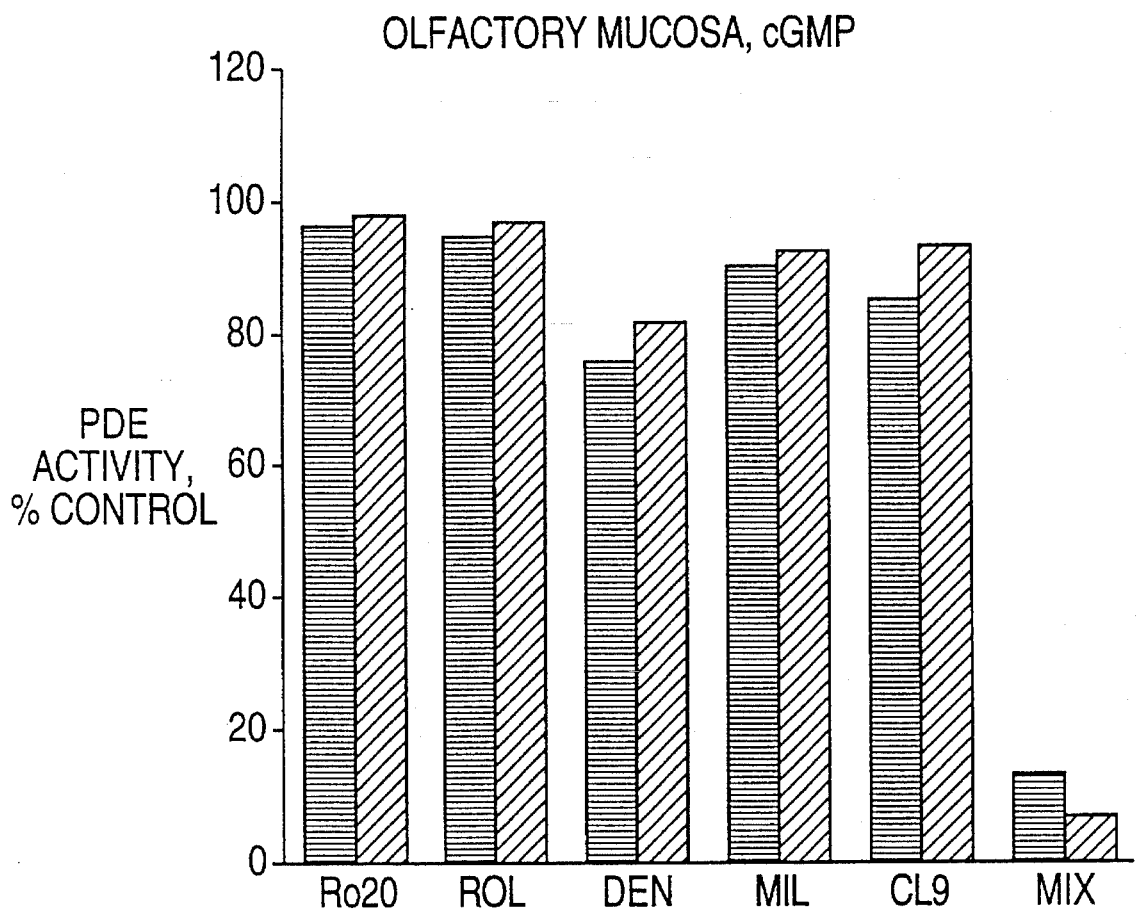
FIG. 1B shows Olfactory mucosa, cGMP PDE activity, assayed at 1 μM cGMP.

It is a discovery of the present inventors that a calcium/calmodulin activated phosphodiesterase (CAM-PDE) is the predominant phosphodiesterase (PDE) in olfactory mucosa. This enzyme is selectively localized to olfactory neurons, and the cilia in particular. The enzyme is distinct in its biochemical properties from other known isoforms of CAM-PDE, such as CAM-PDE from the brain.

Although an antibody raised against brain CAM-PDE (Hansen, et al. (1986) *J. Biol. Chem.*, 261:14636–14645) specifically recognizes olfactory CAM-PDE, antisera to other PDE enzymes do not appreciably immunoreact with olfactory mucosa. These antisera are directed to the cGMP-inhibited PDE, the cGMP-activated PDE, and the retinal rod PDE.

The olfactory CAM-PDE has substantially higher affinity for cAMP than the brain enzyme. Olfactory CAM-PDE has a Km of about 2 μM cAMP, whereas CAM-PDE from the cerebral cortex has a Km of about 40 μM. At physiological concentrations of cAMP (i.e., 1 μM cAMP), the CAM-PDE activity in olfactory cilia is 4–5 times greater than in cerebral cortex. In most mammalian tissues, the predominant CAM-PDE is a low-affinity enzyme (Beavo, et al. (1988) *Advance in Second Messenger and Phosphoprotein Research*, 22:1–38); olfactory CAM-PDE is unusual in its high affinity for cAMP.

It appears that there are other PDEs present in olfactory epithelium. Ro 20-1724 is a selective inhibitor of calcium/calmodulin-independent, high affinity PDE. In the absence of calcium, olfactory PDE is inhibited by Ro 20-1724 about 55%, but in the presence of calcium it is only inhibited about 15%. This suggests that there are at least two PDE enzymes in the olfactory epithelium. The presence of multiple PDE enzymes is consistent with the low Hill coefficient observed for olfactory epithelial PDE.

Olfactory CAM-PDE has been localized to olfactory neurons, particularly the olfactory cilia, by means of immunocytochemistry. This is consistent with the localization to the cilia of other major elements of olfactory transduction, including a selective G protein (Jones, et al. (1989) *Science*, 244: 790–795), olfactory specific adenylyl cyclase (Sklar, et al. (1986) *J. Biol. Chem.*, 261:15538–43; Bakalyar, et al. (1990) *Science*, 250:1403–1406), and a cyclic nucleotide gated ion channel (Nakamura et al. (1987) *Nature*, 325:442–444; Firestein et al. (1989) *Science*, 244:29–82).

According to one embodiment of the invention, an aerosol can be applied to the nose to contact the olfactory epithelium, particularly the olfactory cilia. The aerosol contains an inhibitor of PDE, such as caffeine, papaverine, theophylline, 2-o-propoxyphenyl-8-azapurin-6-one, Vopocetine, TCV-3B and HA588. Other inhibitors of PDE may also be used. These include 7- or 8-alkyl isobutyl methyl xanthone and methyl-3-isobutyl-8-methyl xanthone. Preferably the inhibitor is specific for CAM-PDE and more preferably it is specific for olfactory CAM-PDE. However, this is not required. Specificity of an inhibitor is defined as a ratio of 10-fold higher inhibitory activity of CAM-PDE (CAM-activated PDE) relative to CAM-independent PDE at a particular concentration of inhibitor. Application of CAM-PDE inhibitors leads to enhancement of the sense of smell.

The PDE inhibitor is preferably aerosolized. However, other modes of administration are also possible, such as an ointment, lotion, wash, or inhalable powder.

A device is also provided for enhancing the sense of smell which comprises a nasal nebulizer (or nose sprayer) containing an olfactory PDE inhibitor. The nebulizer aerosolizes the inhibitor, providing a ready means of application to the olfactory epithelium, particularly the olfactory cilia.

In another aspect of the invention, olfactory neuron-derived PDE is used to screen for inhibitor substances. Any enzyme assay known in the art for PDE activity can be used. Similarly, any preparation of olfactory PDE can be used, whether derived directly from animals or cultured cells. Inhibitors of the enzyme activity can be used as smell enhancing agents.

EXAMPLES

Example 1

This example describes the biochemical characterization of PDE activity in olfactory tissue.

1. Calcium/Calmodulin Activation

At least five separate subtypes of PDE have been distinguished on the basis of substrate affinity, activation or inhibition by cGMP, effects of inhibitors, and the influence of $Ca^{2+}$ and calmodulin (Thompson, et al. (1972) *Meth. Enzymol.*, 34:205–212; Kincaid, et al. (1988) *Meth. Enzymol.* 159:457–470; Beavo (1988) *Advances in Second Messenger and Phosphoprotein Research*, 22:1–38). CAM-PDE is selectively stimulated by $Ca^{2+}$ and calmodulin (Teo, et al. (1973) *J. Biol. Chem.*, 248:5950–5955; Sharma, et al. (1986) *Biochem. Cell Biol.*, 64:1072–1080). One form of PDE has high affinity for cAMP and is selectively inhibited by the antidepressant drug rolipram (Thompson et al. (1979) *J. Am. Chem. Soc.*, 79:5228–5237; Wachtel (1983) *Neuropharmacol.*, :267–272; Nemoz, et al., (1989) *Eur. J. Biochem.*, 184:511–520). Another form with high affinity for cAMP is activated by cGMP (Beavo et al. (1971) *J. Biol Chem.*, 246:3841–3846; Martins, et al. (1982) *J. Biol. Chem.*, 257:1973–1979; Yamamoto et al. (1983) *J. Biol. Chem.*, 258:12526–12533) while a third form selective for cAMP is inhibited by cGMP (Weber, et al. (1982) *J. Biol. Chem.*, 257:5339–5341; Harrison et al., (1986) *Mol. Pharmaco.*, 29:506–514; Simmons, et al. (1988) *Mol. Pharmacol.*, 33:664–671). The retina possesses a PDE with considerable selectivity for cGMP (Miki, et al. (1973) *Proc. Natl. Acad. Sci. USA*, 70:3820–3824). In initial experiments, we explored the biochemical properties of PDE activity in homogenates of olfactory mucosa (prepared as described below) (Table 1). Using 1 μM cAMP or 1 μM cGMP in the presence of 100 μM $Ca^{2+}$, basal PDE activity in mucosal homogenates is threefold higher than with 100 μM EGTA. Calmodulin further enhances the stimulation of enzyme activity by $Ca^{2+}$.

TABLE 1

Effects of Ca++ and Calmodulin on Olfactory Phosphodiesterase Activity

| | Cilia | | Olfactory Mucosa | |
|---|---|---|---|---|
| | cAMP | cGMP | cAMP | cGMP |
| | Specific Activity (nmol/mg/min) | | | |
| Control | 2.1 (5) | 1.4 (3) | 0.47 (3) | 0.16 (2) |
| 100 μM $Ca^{2+}$ | 3.1 (3) | 2.2 (1) | 1.5 (2) | 0.33 (1) |
| 100 μM $Ca^{2+}$ and 50 nM Calmodulin | 5.5 (5) | 3.8 (3) | 1.6 (3) | 0.68 (2) |

Data presented are means of n independent experiments performed in duplicate with n indicated in parentheses. Values varied by less than 20%.

PDE assays employed the method of Thompson et al. (1972) *Meth. Enzymol.* 34:205–212, as modified by Bauer and Schwabe (1980) *Naunyn-Schmiedeberg's Arch. Pharmacol.*, 311:193–198, with standard reaction mixture adapted from Kincaid and Maganiello (1988) *Meth. Enzymol.*, 159:457–470. Before use, [³H]cAMP (NEN-DuPont, Boston, Mass.) was purified over QAE-Sephadex (Pharmacia, Piscataway, N.J.). Reaction mixture (200 μl) containing 60,000–80,000 cpm [³H]cAMP were added to test tubes and prewarmed to 37° C. Tissue was warmed to 37° C. and 100 μl aliquots containing 1–2 μλ protein added to initiate the assay which was conducted for 20 minutes at 37° C. Final concentrations in the incubation mixture were: 50 mM BES N,N-bis-(2-hydroxyethyl)-2-amino-ethane-sulfonic acid), 5 mM M $Cl_2$, 0.2 mg/ml BSA, 0.78–200 μM unlabeled cAMP (Sigma, St. Louis, Mo.), and 0.1 mM EGTA. For experiments at 100 μM free $Ca^{2+}$, the reaction mix included 0.2 mM $CaCl_2$ and 50 nM calmodulin (Sigma) where appropriate. Low $Ca^{2+}$ conditions were achieved by addition of 2.0 mM EGTA. $Ca^{2+}$ levels were measured against standards using a conductivity meter and $Ca^{2+}$ electrode (Biomedical Instrumentation Group, Philadelphia, Pa.). Following incubation, reactions were stopped by boiling for 1.5 minutes and cooling on ice, whereupon 100 μl aliquots of 5'-nucleotidase (10 units/ml in 0.1M Tris pH 8.1) were added and samples incubated for 30 minutes at 37° C. Incubation mixtures were applied to QAE-Sephadex columns pre-equilibrated with 30 mM ammonium formate, with flow through and eluate from two 1 ml washes collected in plastic scintillation vials. Ten ml formula 963 (DuPont, Wilmington, Del.) were added and radioactivity assessed in a Beckman LS 3801 counter (Irvine, Calif.). Assays of cGMP PDE were performed similarly, except that cGMP was used in place of cAMP, and columns were eluted with 3 ml wash volume.

Tissue was prepared either as cilia, using the method of Sklar et al., (1986), or as homogenates of olfactory turbinates or cerebral cortex.

2. Selective Inhibition of PDE Activity

Selective inhibitors of PDE were used to distinguish isoforms. Hydrolysis of both cAMP and cGMP in olfactory mucosa and cilia was assayed under $Ca^{2+}$ chelating conditions or in the presence of 100 μM $Ca^{2+}$ (FIG. 1).

Ten μM rolipram (Schering AG, Berlin, Germany), 10 μM Ro20-1724 (Biomol Research Laboratories, Plymouth Meeting, Pa.) and 10 μM denbufylline (Smith-Kline Beecham, Betchworth, U.K.) inhibit cAMP hydrolysis by 49, 66 and 64%, respectively when PDE activity in olfactory mucosa is assayed in the presence of 100 μM EGTA and no added $Ca^{2+}$ (FIGS. 1A, B). Neither 10 μM rolipram nor 10 μM Ro20-1724 inhibit cGMP hydrolysis, while 10 μM denbufylline inhibits cGMP hydrolysis only about 20%. These three drugs have been reported to selectively inhibit the high affinity cAMP-selective form of PDE (Epstein et al. (1982) *Arch. Biochem. and Biophys.*, 218:119–133; Wachtel (1983) *Neuropharmacol.*, 22:267–272; Nicholson, et al. (1989) *Br. J. Pharmacol*, 97:889–897).

The cardiotonic drugs milrinone (10 μM; Winthrop Research Institute, Renasselaer, N.Y.) and Cl 930 (10 μM; Warner-Lambert/Parke-Davis, Ann Arbor, Mich.), selective for cGMP-inhibited PDE (Harrison et al. (1986) *Mol Pharmacol.*, 29:506–514; Kincaid and Manganiello (1988) *Meth. Enzymol.* 159:457–470), reduce PDE activity about 30% in the presence of 100 μM EGTA and about 15% with 100 μM $Ca^{2+}$. In cilia, neither rolipram (10 μM) nor Ro20–1724 (10 μM) inhibit PDE, whether assayed in the presence or absence of $Ca^{2+}$. Denbufylline (10 μM) inhibits both ciliary cAMP and cGMP PDE 15–20% in the presence or absence of $Ca^{2+}$. Less than 10% inhibition occurs with 10 μM milrinone or 10 μM CI 930 in cilia regardless of assay conditions.

Figure 2:
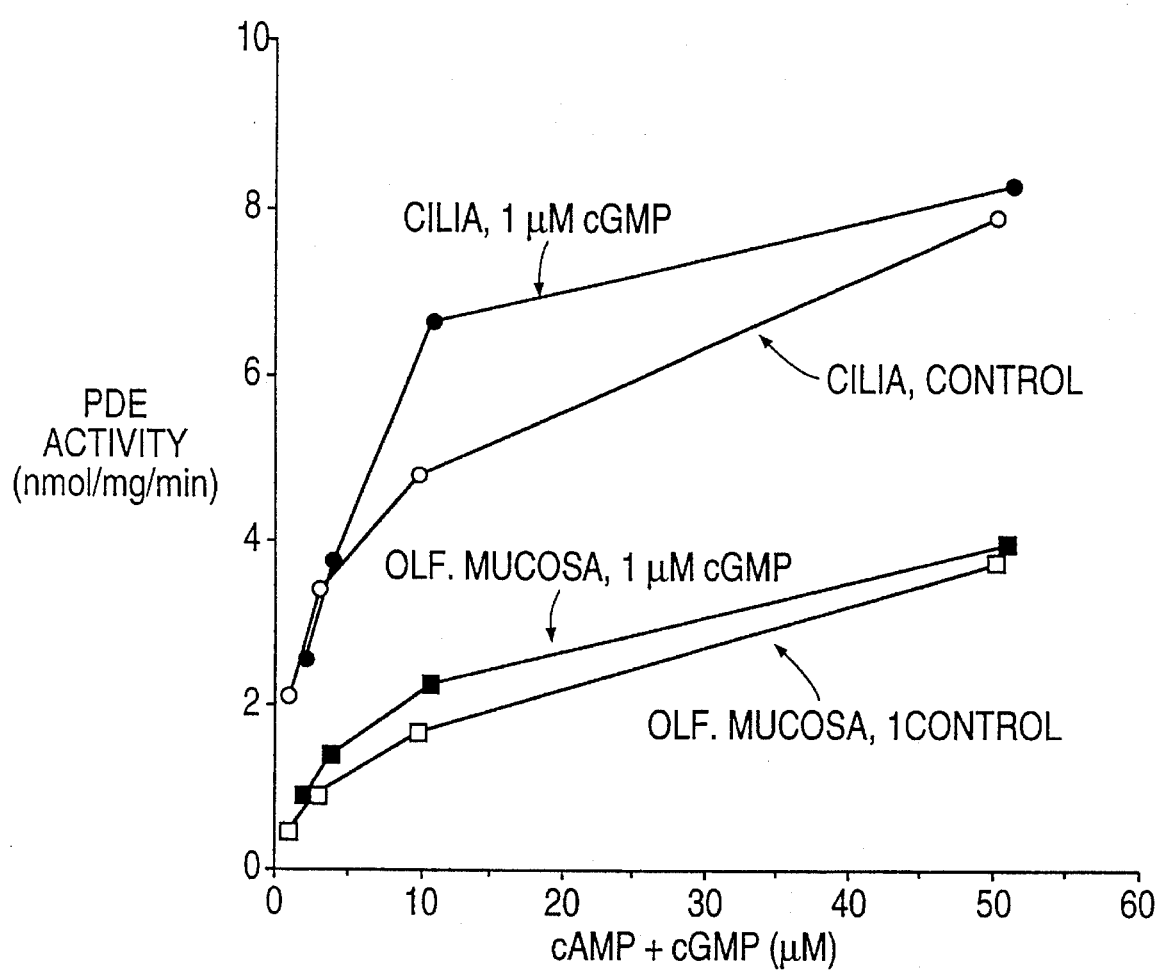
FIG. 2 demonstrates the effect of 1 μM cGMP on PDE activity. Activity is graphed as a function of total cyclic nucleotides present using olfactory cilia, or mucosa with 1 μM cGMP.

We also examined the effect of 1 μM cGMP on cAMP PDE activity (FIG. 2). In both cilia and olfactory mucosa cGMP stimulates cAMP hydrolysis to a limited extent, with a maximal 20–30% enhancement at 10 μM cAMP, in the presence of 100 μM EGTA. This effect diminishes markedly when $Ca^{2+}$ and calmodulin are added, suggesting that cGMP stimulated PDE is much less abundant than CAM-PDE.

These results suggest the presence of at least three forms of PDE in the olfactory mucosa, the two predominant ones being CAM-PDE and the rolipram inhibitable PDE with high affinity for cAMP. PDE forms regulated by cGMP may be present to a lesser extent. We do not detect any cGMP selective enzyme. In washed cilia, CAM-PDE appears to be the predominant PDE.

3. Kinetic Analysis of PDE Activity

Figure 3A:
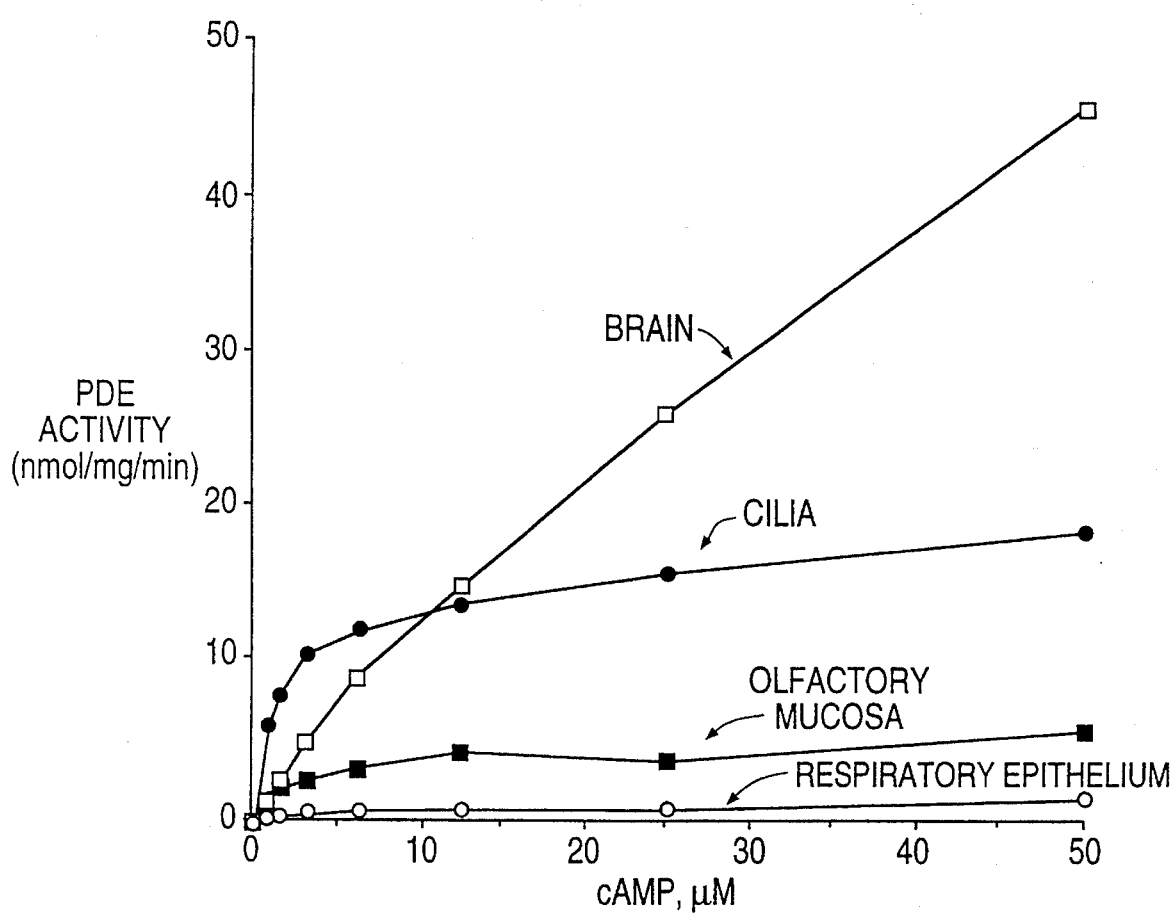
FIG. 3A is a Direct plot of enzyme activity versus cAMP concentration for olfactory mucosa, cilia, cerebral cortex, and respiratory epithelium.
Figure 3B:
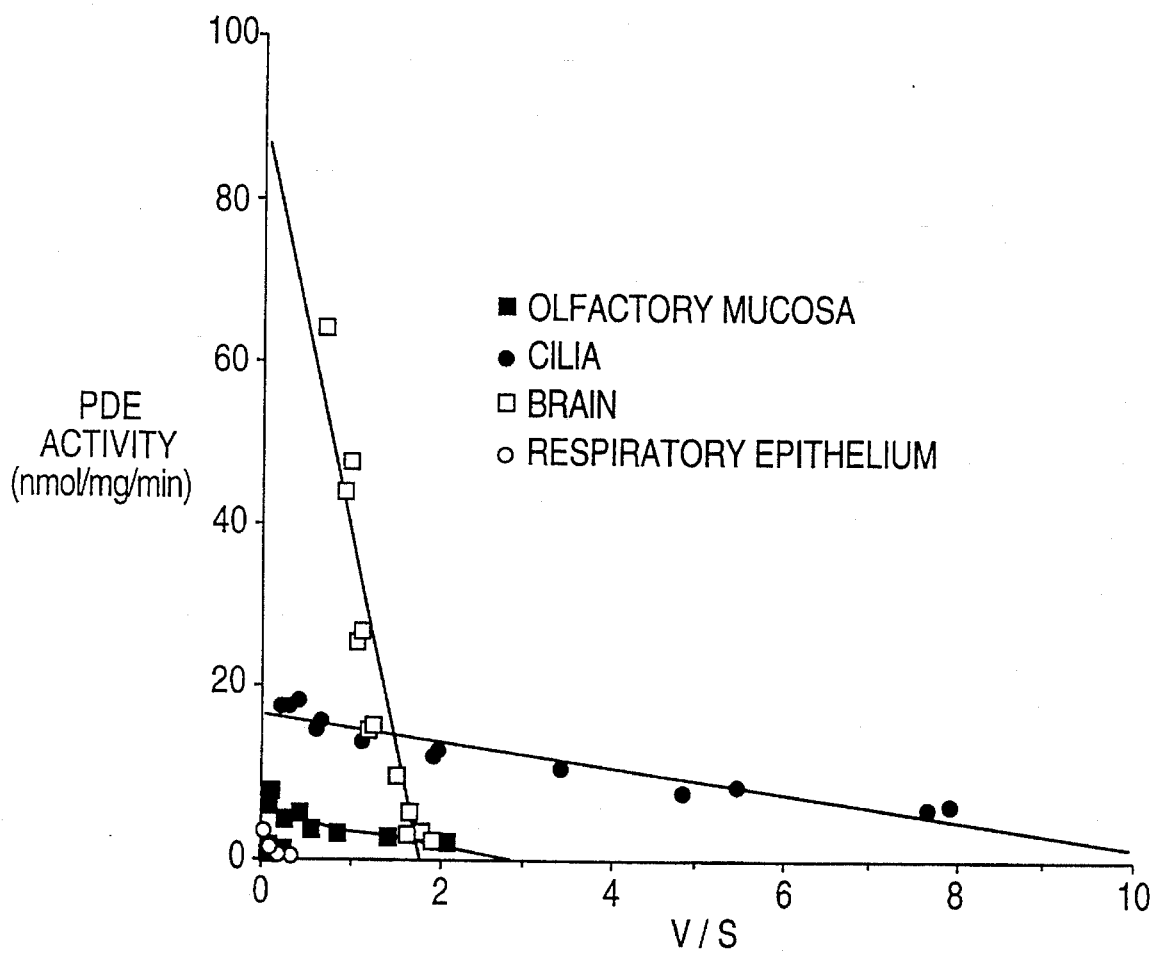
FIG. 3B is a Eadie Hofstee analysis of enzyme activity (nmol/mg/min) versus activity divided by substrate concentration (μM).

We examined PDE activity with a wide range of cAMP concentrations in olfactory cilia, olfactory mucosa and respiratory epithelium and brain homogenates (FIG. 3; Table 2). Olfactory cilia display the highest affinity for cAMP, as is evidenced in a direct plot of enzyme activity versus cAMP concentration (FIG. 3A) as well as in an Eadie-Hofstee analysis (FIG. 3B). By contrast, the highest maximal velocity occurs in brain tissue with a $V_{max}$ more than five times that of cilia. At low micromolar concentrations of cAMP, on the other hand, ciliary PDE activity is three-to-five times greater than in the brain. Maximal enzyme activity in olfactory mucosa is more than double that of respiratory epithelium. In studies of primary cultures of olfactory receptor neurons, which possess odorant stimulated adenylyl cyclase activity (Ronnett et al. (1991) *J. Neurosci.*, 11:1243–1255; *Proc. Natl. Acad. Sci. USA*, 88:2366–2369), the Km for cAMP is 2.2 μM, about the same as in olfactory mucosa while the $V_{max}$ is 1.25 nmol/mg/min, similar to that of respiratory epithelium.

TABLE 2

Kinetic Constants of Phosphodiesterase Activity in Nasal and Brain Tissue

| | Olfactory Mucosa | Olfactory Cilia | Cerebral Cortex | Respiratory Epithelium |
|---|---|---|---|---|
| Km (μM) | 2.2 | 1.5 | 43.0 | 5.1 |
| $V_{max}$ (nmol/mg/min) | 4.9 | 14.0 | 74.0 | 2.1 |
| Hill Coefficient | 0.48 | 0.52 | 0.93 | 0.47 |
| V (at 1 μM cAMP) | 1.6 | 5.6 | 1.8 | 0.40 |

PDE assay was performed with 100 μM $Ca^{2+}$ and calmodulin as described above. Km and $V_{max}$ were calculated from Eadie Hofstee plots based on the best fit lines. Hill coefficients were calculated from plot of log (V/(1-V)) vs. log [cAMP].

$Ca^{2+}$ and calmodulin produce their greatest stimulation of PDE activity at low (1 μM) cAMP levels with 3.5–4.0 fold enhancement in olfactory epithelium, cilia and brain and somewhat lesser stimulation in respiratory epithelium and primary olfactory neuronal cultures. Unlike the low-affinity brain CAM-PDE, which has a Km of approximately 40 μM, olfactory CAM-PDE appears to be a high affinity enzyme, with a Km of approximately 2 μM. These results suggest that the olfactory CAM-PDE may be a different enzyme than that found in brain.

The Hill coefficient for PDE activity is almost 1 in brain, 0.5–0.6 in cilia and respiratory epithelium, and only about 0.4 in olfactory epithelium. These low Hill coefficients most likely reflect the presence of multiple populations of PDE with differing affinities foe cAMP rather than negative cooperativity of the enzyme.

Figure 4A:
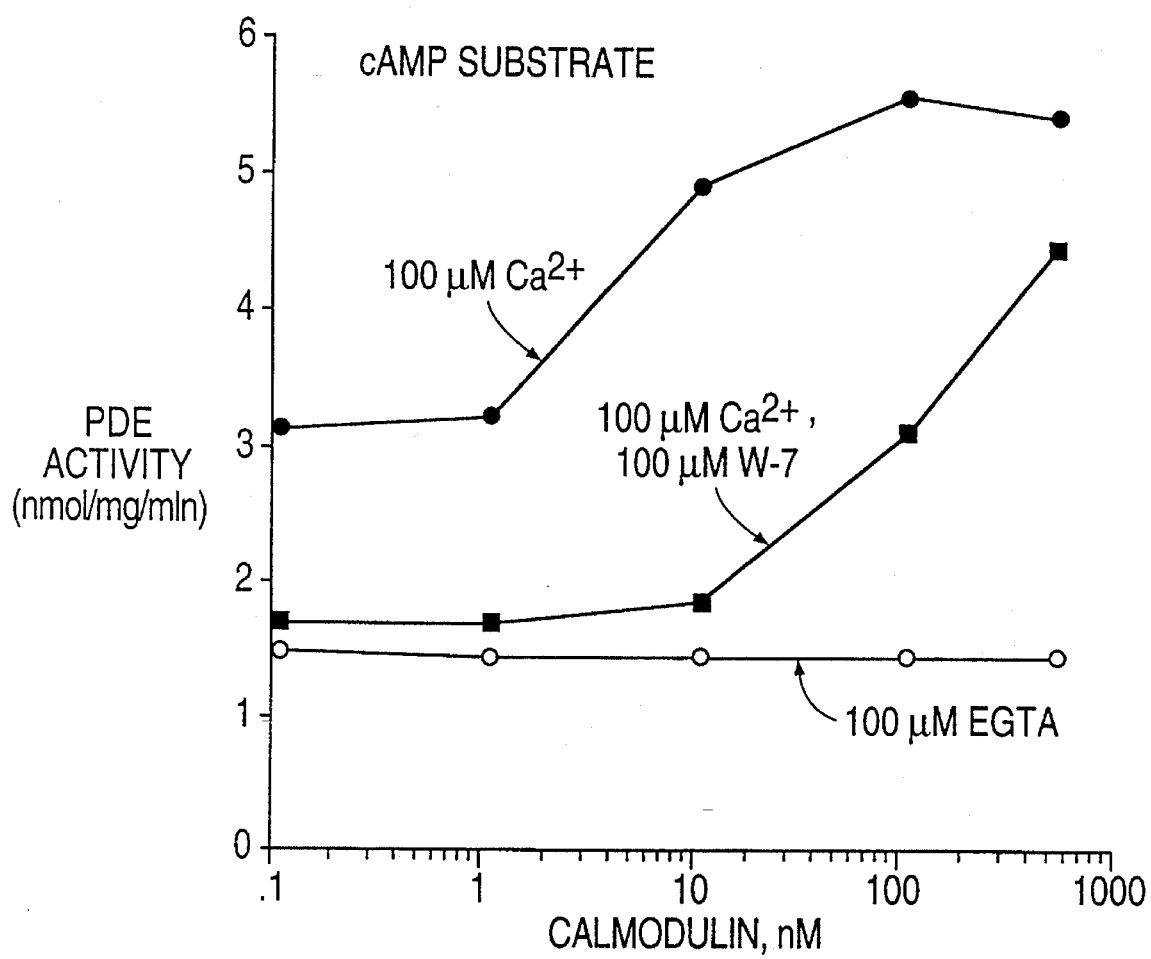
FIG. 4A is a graph of activity with, 1 μM cAMP used as substrate: 100 μM EGTA (open circles); 100 μM Ca$^{2+}$ (filled circles); 100 μM Ca$^{2+}$ in the presence of 100 μM W-7 (filled squares).
Figure 4B:
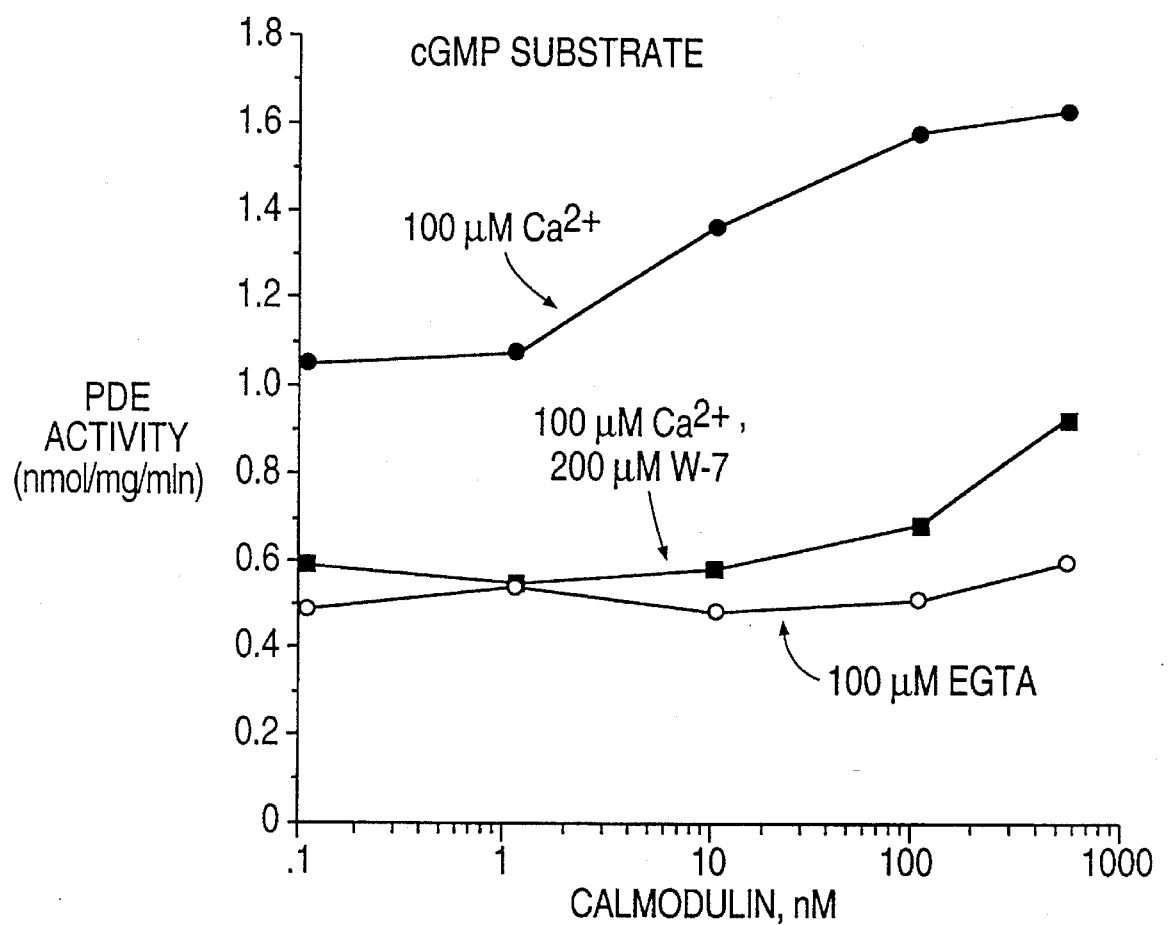
FIG 4B is a graph of activity, 1 μM cGMP used as substrate: 100 μM EGTA (open circles); 100 μM Ca$^{2+}$ (filled circles); 100 μM Ca$^{2+}$ in the presence of 200 μM W-7 (filled squares).

PDE activity in cilia is markedly stimulated by calmodulin (FIG. 4). At 1 μM cAMP or cGMP half maximal stimulation by calmodulin is apparent at 10 nM. Enzyme activity is 2–3 fold higher with cAMP than cGMP at all concentrations of calmodulin. The calmodulin antagonist W-7 (Gibco BRL, Gaithersburg, Md.) substantially reduces stimulation by calmodulin, while raising the concentration of calmodulin from 0.1 nM to 1 μM progressively augments both cAMP and cGMP PDE activity, consistent with competition between calmodulin and W-7.

Example 2

This example demonstrates that olfactory mucosa PDE is associated with olfactory neurons.

To examine an association of olfactory mucosal PDE with olfactory neurons, we evaluated the effects of olfactory bulbectomy. Destruction of the olfactory bulb causes retrograde degeneration of olfactory receptor neurons in the olfactory mucosa (Margolis et al. (1974) *Brain Research*, 81:469–483). Bulbectomies were performed unilaterally permitting comparison of normal and denervated sides. Adult male rats, 150–200 g, were anesthetized with chloral hydrate (0.5 g/kg, ip) and placed in a stereotaxic head holder. A single 2 cm midline incision was made starting midway between the eyes. The dura on the right side was scraped to bare the bone. A hole was drilled through the bone directly above the olfactory bulb. A narrow glass pipet was placed in the hole and suction gently applied. In a successful bulbectomy, the bulb could be seen as a white mass during aspiration. After reaching bone, aspiration was complete. The hole was packed with gel foam, and skin closed with surgical staples. Rats were kept warm while recovering, allowed to awaken naturally, then returned to animal holding facilities until needed 10–11 days later.

The efficacy of bulbectomy was ensured in several ways. When the site of bulbectomy is directly inspected only about 10% of olfactory bulb tissue remains. Histochemical examination of the olfactory epithelium reveals a marked depletion of olfactory neurons (FIG. 5). Moreover, staining for olfactory marker protein (Margolis et al., 1974) is depleted about 80% (data not shown).

As shown in Table 3, in olfactory epithelium from control animals, about 75% of total PDE activity measured in the presence of EGTA occurs in the soluble supernatant fraction with 13% each in the microsomal ($P_3$) and denser particulate ($P_2$) fractions. Stimulation by $Ca^{2+}$ and calmodulin is greatest in the $P_3$ and $P_2$ fractions. In the presence of $Ca^{2+}$ and calmodulin, only 50% of PDE activity is soluble, while 20%–25% occurs in each of the $P_3$ and $P_2$ fractions. Following bulbectomy, PDE specific activity is depleted by about 90% and 80% in the $P_2$ and $P_3$ fractions, respectively, while soluble specific activity is diminished only about 50%. Total soluble activity is not significantly changed following bulbectomy. Depletion is greatest for $Ca^{2+}$/calmodulin stimulated activity, but still pronounced when measured in the presence of EGTA.

TABLE 3

Subcellular Distribution of Phosphodiesterase Activity in Control
and Bulbectomized Olfactory Mucosa

| | DENSE PARTICULATE (P2) | | MICROSOMAL (P3) | | SOLUBLE (S3) | |
|---|---|---|---|---|---|---|
| | Specific Activity nmol/mg/min | Units pmol/min | Specific Activity nmol/mg/min | Units pmol/min | Specific Activity nmol/mg/min | Units pmol/min |
| CONTROL | | | | | | |
| $Ca^{2+}$ | 1.78 ± 0.35 | 182 ± 62 | 1.16 ± 0.87 | 148 ± 45 | 0.96 ± 0.39 | 368 ± 83 |
| EGTA | 0.46 ± 0.02 | 48 ± 11 | 0.41 ± 0.24 | 38 ± 8 | 0.65 ± 0.32 | 222 ± 46 |
| BULBECTOMIZED | | | | | | |
| $Ca^{2+}$ | 0.15 ± 0.02 | 36 ± 8 | 0.15 ± 0.07 | 51 ± 20 | 0.52 ± 0.28 | 404 ± 150 |
| EGTA | 0.08 ± 0.02 | 19 ± 3 | 0.09 ± 0.04 | 28 ± 11 | 0.18 ± 0.06 | 172 ± 71 |

PDE assays were performed using 1 μM cAMP in the presence of 50 nM calmodulin and 100 mM $Ca^{2+}$ or 2 mM EGTA. Results are expressed as mean ± S.E.M. of 3–4 independent experiments performed in duplicate.

Subcellular fractions were obtained as described below. Rats were anesthetized with carbon dioxide, decapitated and tissue dissected. Nasal turbinates were dissected intact and consisted of the entire olfactory mucosa, including endothelial tissue, olfactory epithelium, and overlying mucous. Tissue was immediately placed on ice in BES homogenization buffer (BHB) containing 50 mM N,N-bis-(2-hydroxyethyl)-2-aminoethanesulfonic acid (BES) (Calbiochem, La Jolla, Calif.), 0.1M EGTA, 0.08 mg/ml dithiothreitol (DTT), 0.1 mg/ml phenylmethylsulfonyl fluoride (PMSF), 0.5 μg/ml antipain, 1 μg/ml leupeptin, 1 μg/ml aprotinin, 0.6 μ/ml chymostatin, 0.6 μg/ml pepstatin, 0.06% DMSO, 0.1% ethanol, and homogenized 15 times up and down in a glass-Teflon homogenizer at setting 3.3 of the Wheaton overhead stirrer (Millville, N.J.). For fractionation, tissue was first centrifuged at 500×g for 5 minutes in a Sorvall RC 2B superspeed refrigerated centrifuge (DuPont, Wilmington, Del.). The crude particulate (P1) pellet was discarded and the supernatant (S1) centrifuged 20 minutes at 28,000×g. The resultant pellet (P2) was washed in BHB, centrifuged and resuspended in 5 ml BHB, and designated the membrane fraction. The supernatant (S2) was centrifuged 50 minutes at 230,000×g in Beckman L8-M ultracentrifuge (Fullerton, Calif.). The pellet (P3) was washed in BHB, recentrifuged in an ultracentrifuge, and resuspended in 2 ml BHB as the microsomal fraction. The supernatant (S3) was saved as the soluble fraction and visually inspected for absence of cloudiness or lipid droplets. In all cases, protein was assayed by the Bradford method using Coomassie Protein Assay Reagent (Pierce, Rockford, Ill.) and BSA as standard.

Example 3

This example demonstrates that CAM-PDE is localized to the cilia, neuronal cell bodies, dendritic knobs, and axon bundles.

We have conducted immunohistochemical studies utilizing a monoclonal antibody with high affinity for CAM-PDE of rat brain and 100 times less affinity for calmodulin itself or other calmodulin binding proteins (Hansen, et al. (1986) *J. Biol. Chem.*, 261:14636–14645).

Adult male rats (150–200 g) were anesthetized with pentobarbital sodium (45 mg/kg, ip) (Steris Laboratories, Phoenix, Ariz.) and perfused transcardially with phosphate buffered saline (PBS) followed by 4% paraformaldehyde (PFA) in PBS. Brain and olfactory tissues were dissected and postfixed 1 hour in 4% PFA, then sunk in 15% (w/v) sucrose overnight. Blocks were embedded in tissue-tek (Miles, Elkhart, Ind.) and stored at −70° C. until use, then sectioned in a cryostat at 12 μm.

Staining was carried out using a modification of the method described by Ronnett, et al. (1991) *J. Neurosci.*, 11:1243–1255). Brain and olfactory tissue sections were rinsed three times in PBS with all subsequent rinses performed identically, then permeabilized for 30 minutes in 0.5% (w/v) saponin in PBS or 0.1% (w/v) Triton-X-100 in PBS, respectively. Slides were rinsed and incubated 1 ; hour in 10% (v/v) normal goat serum (NGS) (Jackson Labs, Westgrove, Pa.) or 10% (v/v) normal donkey serum (NDS) (Jackson Labs, Westgrove, Pa.), as appropriate to the secondary antibody, in PBS containing 1% (w/v) bovine serum albumin (BSA). Following removal of the block, slides were incubated with primary antibody made up in PBS containing 0.5% (w/v) BSA and 2% (v/v) NGS or NDS as appropriate. Slides were rinsed and incubated 25 minutes in PBS containing 0.3% (v/v) hydrogen peroxide to quench endogenous peroxide. Slides were rinsed again, then blocked in 5% (v/v) NGS or NDS in PBS containing 0.5% BSA. After block removal, slides were incubated 45 minutes with the appropriate biotinylated secondary antibody in PBS containing 0.5% (w/v) BSA. Slides were rinsed, blocked 5 minutes in PBS containing 0.5% (w/v) BSA, and incubated 30 minutes with 2 μg/ml peroxidase conjugated streptavidin (Jackson Labs, Westgrove, Pa.). Slides were rinsed in PBS and then exposed 5 minutes to the chromagen 3,3-diaminobenzidine tetrahydrochloride (DAB) (GIBCO BRL, Gaithersburg, Md.). Slides were dehydrated with progressive ethanol gradations followed by xylene, and coverslipped.

Antisera were used as follows: mouse monoclonal antibody (MAb) ACC-A4C3 against $Ca^{2+}$/calmodulin dependent phosphodiesterase (CAM-PDE) (Hansen, et al. (1986) *J. Biol. Chem.*, 261:14636–14645) at 1:250 dilution; affinity purified sheep polyclonal antibody to calmodulin (Polysciences, Inc., Warrington, Pa.) at 1:10 dilution; goat anti-mouse IgG biotinylated secondary antibody (Jackson Labs, Westgrove, Pa.) at 1:500 dilution; donkey anti-sheep biotinylated secondary antibody (Jackson Labs, Westgrove, Pa.) at 1:500 dilution.

Specificity of the antibody reaction was established in several ways. Staining was negative when non-immune ascites fluid was used in place of primary antibody. Similarly, no staining was obtained with only NGS or NDS. The ability of MAb ACC-A4C3 to immunoprecipitate PDE activity when coupled to formalin fixed Staph A was examined using the method of Hansen, et al. (1986) *J. Biol. Chem.*, 261:14636–14645). Antibody conjugated Staph A and Staph A controls were incubated with soluble or microsomal tissue fractions overnight, then centrifuged 3 minutes at 10,000 g. After extensive washing, the pellets were assayed for PDE activity. In both cases, the antibody precipitated threefold more PDE activity than Staph A alone. Precipitated PDE activity was doubled in the presence of $Ca^{2+}$ and calmodulin.

Figure 5A:
FIG. 5 shows immunohistochemical localization of CAM-PDE in olfactory turbinates. Panel A, Immunoreactivity (IR) of MAb ACC-A4C3 against CAM-PDE is shown at 200×magnification, using Nomarski optics. IR is present in olfactory neuron cell bodies, dendritic knobs, cilia and olfactory nerve bundles. No IR is present in either the sustentacular (sus.) or basal cell layers. Panel B, IR of sheep polyclonal Ab against calmodulin shown at 200×magnification, using Nomarski optics. IR is present in olfactory neuron cell bodies, dendritic knobs and nerve bundles, but not in cilia. Panel C, 1000×magnification oil immersion phase image of CAM-PDE IR shows dense staining in dendritic knobs and cilia as well as soma. Arrowheads indicate dendritic knobs and cilia clearly exhibiting positive IR. Abbrev.: Olfactory neuron (ON). Panel D, Control photomicrograph at 200×magnification, using Nomarski optics shows very little IR. MAb ACC-A4C3 against CAM-PDE was preabsorbed with a five-fold molar excess purified CAM-PDE from bovine brain (61 kD and 63 kD forms) for 1 hour prior to immunostaining. Almost all IR was eliminated.
Figure 5B:
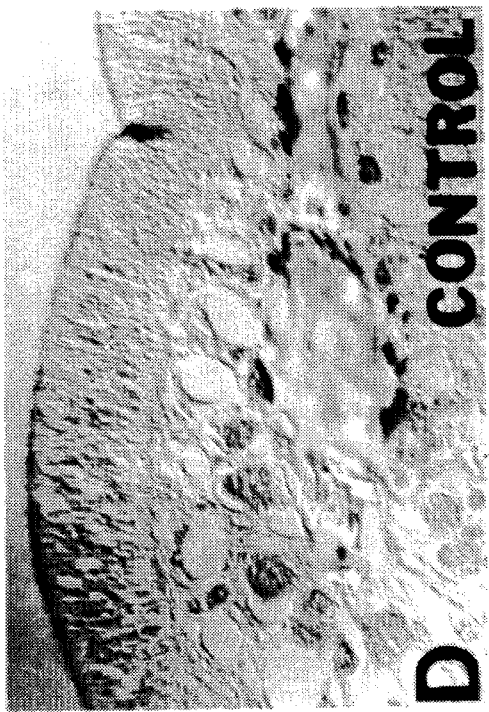
Figure 5C:
Figure 5D:
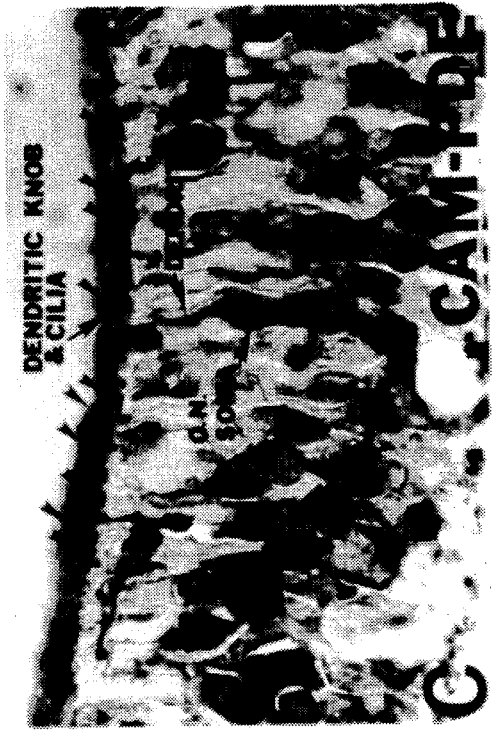

At low magnification staining for CAM-PDE is most prominent in the ciliary layer but is also apparent in neuronal cell bodies and axon bundles (FIG. 5A). At higher power, we can determine that staining of the ciliary layer is due to immunoreactivity within the cilia as well as the dendritic knobs (FIG. 5C). In contrast, staining with an antibody which specifically recognizes calmodulin (Dedman, et al. (1978) *J. Biol. Chem.*, 253:7515–7521), shows immunoreactivity in cell bodies, axon bundles and dendritic knobs, but not in cilia (FIG. 5B). Specificity of the CAM-PDE antibody is demonstrated by preabsorption with the 61 K and 63 K forms of bovine CAM-PDE eliminating almost all staining (FIG. 5D). Antisera to the cGMP-inhibited and the retinal rod PDE enzymes also give no staining. Antisera to the cGMP-stimulated PDE do not stain olfactory receptor neurons, but specifically stain goblet cells.

Figure 6A:
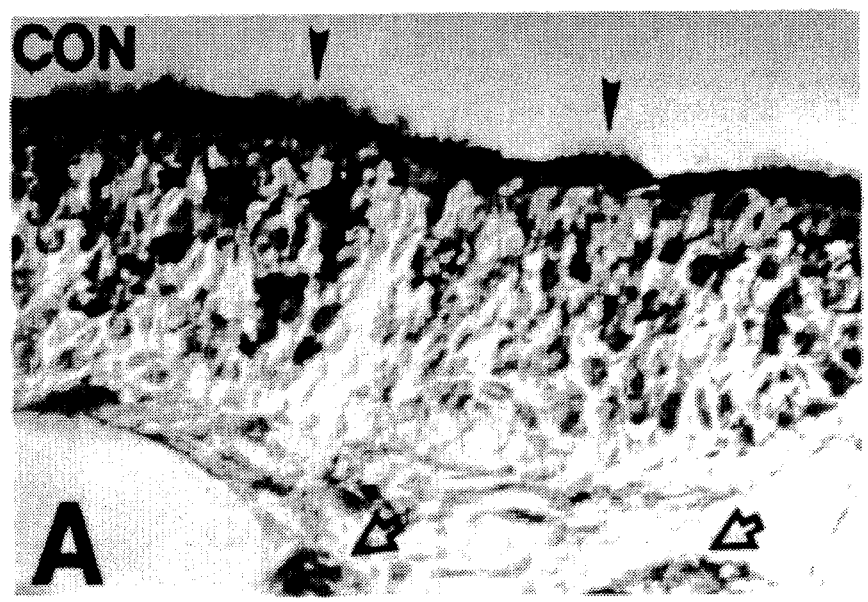
FIG. 6 compares immunohistochemical localization of CAM-PDE in control and bulbectomized turbinates. CAM-PDE immunoreactivity was visualized by Nomarski optics and magnified 620×. Panel A, control epithelium: filled arrowheads indicate positive IR in clumps of cilia, while open arrows show IR in olfactory nerve bundles. Panel B, bulbectomized epithelium: cilia cannot be easily seen. Filled arrowheads indicate positive IR in dendritic knobs which have not yet reached the epithelial surface. Open arrows show IR in olfactory nerve bundles.
Figure 6B:
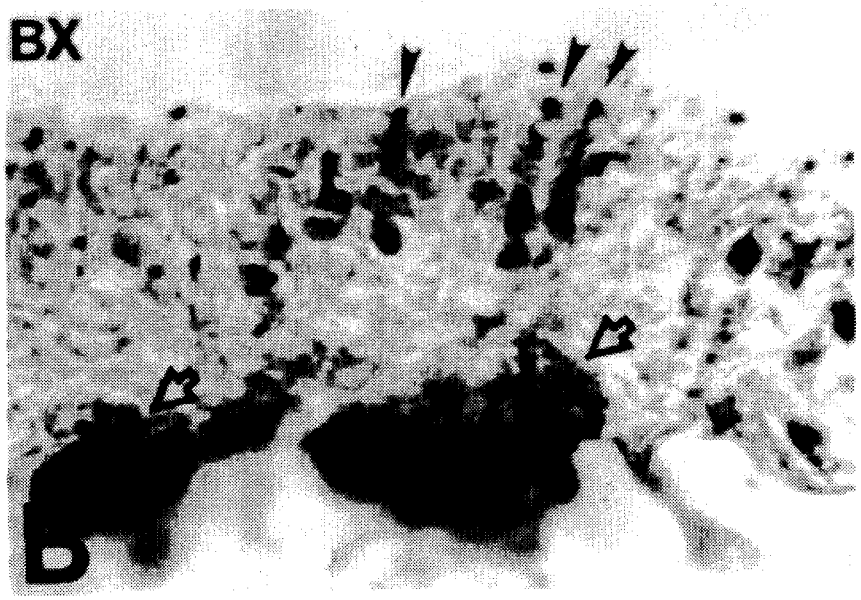
Figure 7:
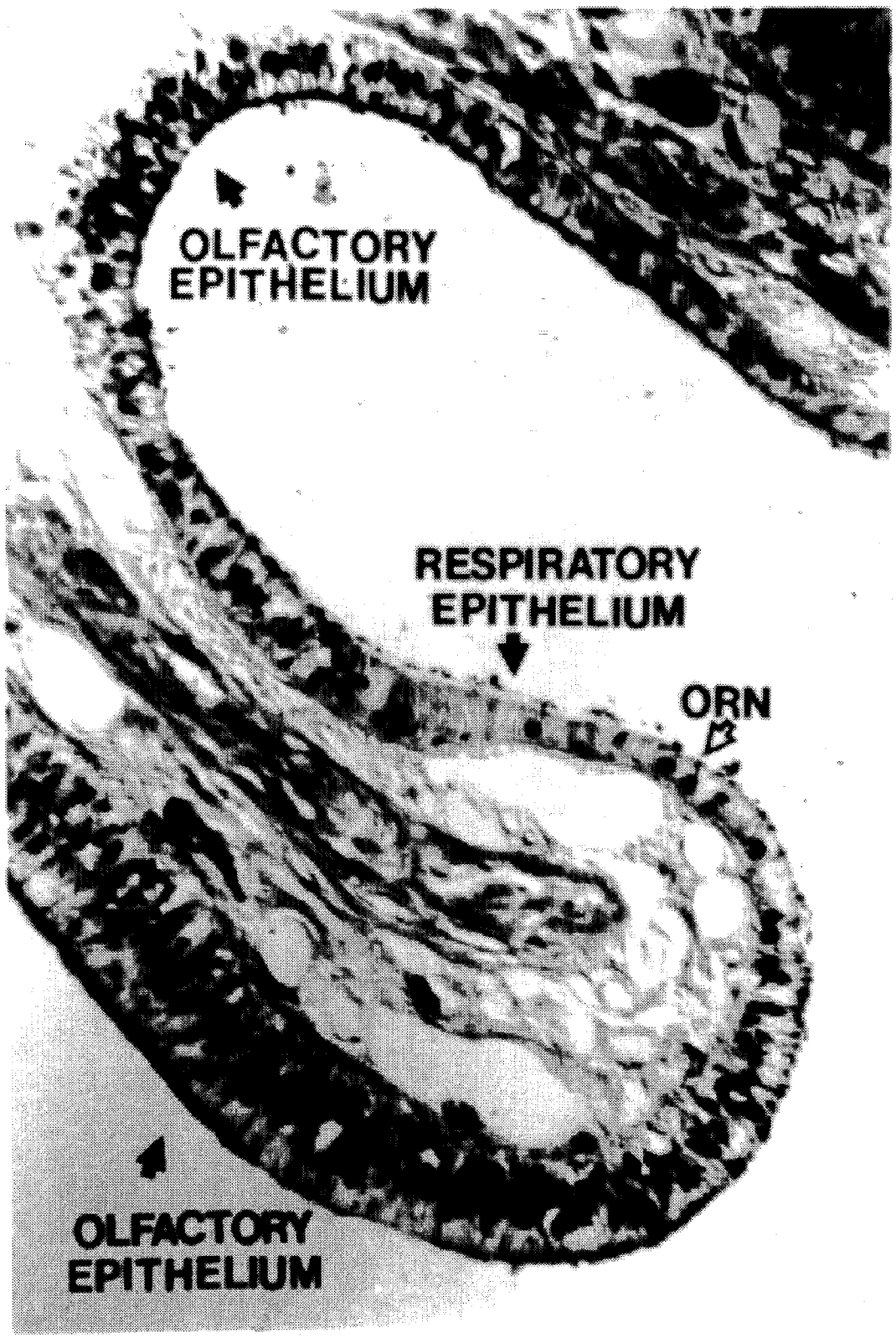
FIG. 7 shows the immunohistochemical localization of CAM-PDE at region of overlap between olfactory and respiratory epithelium. CAM-PDE immunoreactivity was visualized by Nomarski optics and is shown at 250×magnification. Only olfactory receptor neurons exhibit immunoreactivity to Mab ACC-A4C3 against CAM-PDE. Respiratory epithelial cells and respiratory cilia remain unstained. Areas of olfactory epithelium and respiratory epithelium are marked by arrows. Open arrow indicates an isolated olfactory receptor neuron (ORN).

We observe marked differences in olfactory epithelial staining between normal and bulbectomized sides (FIG. 6). The extremely intense staining of the ciliary layer in the intact side (FIG. 6A) is absent in the bulbectomized side (FIG. 6B). By contrast, in the bulbectomized side, neuronal cell bodies stain to a greater extent than in the intact side, presumably reflecting cells surviving bulbectomy or regenerating cells. The dendritic processes of the stained cells in the bulbectomized side tend not to reach the ciliary layer, suggesting that these represent regenerating olfactory neuronal cells. Loss of ciliary staining following bulbectomy is not solely due to deciliation. CAM-PDE immunoreactivity appears to be selective for olfactory neurons. By comparison, respiratory epithelial cells and cilia are not stained by this antibody (FIG. 7).

Figure 8A:
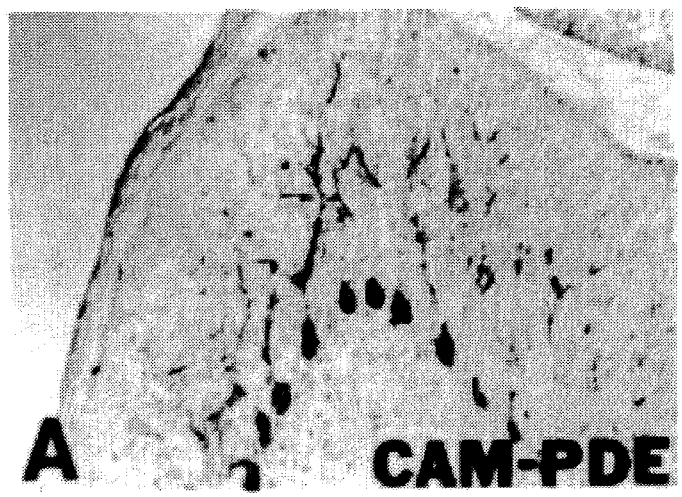
FIG. 8 shows immunohistochemical localization of CAM-PDE in cerebellum. Immunoreactivity is visualized by Nomarski optics and is shown at 130×magnification. Panel A, MAb ACC-A4C3 against CAM-PDE exhibits IR selectivity in Purkinje cells and their processes. Panel B, sheep polyclonal Ab against calmodulin shows IR in Purkinje cells and, to a lesser extent, granule cells. Panel C, preabsorption of MAb ACC-A4C3 with a five-fold molar excess of purified CAM-PDE eliminates IR, demonstrating specificity of the antibody.
Figure 8B:
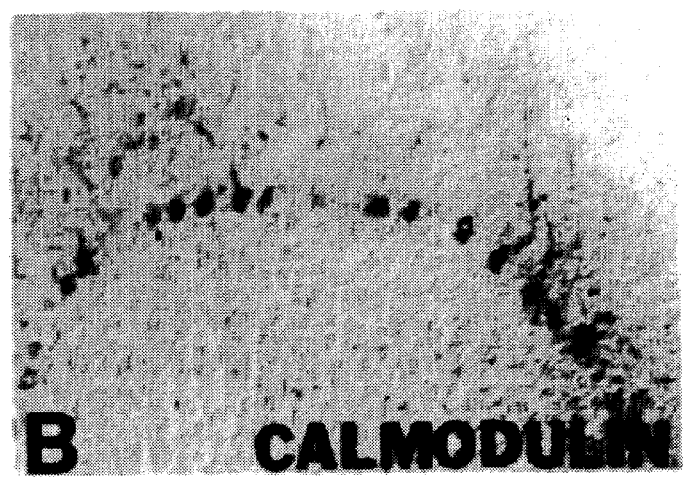
Figure 8C:
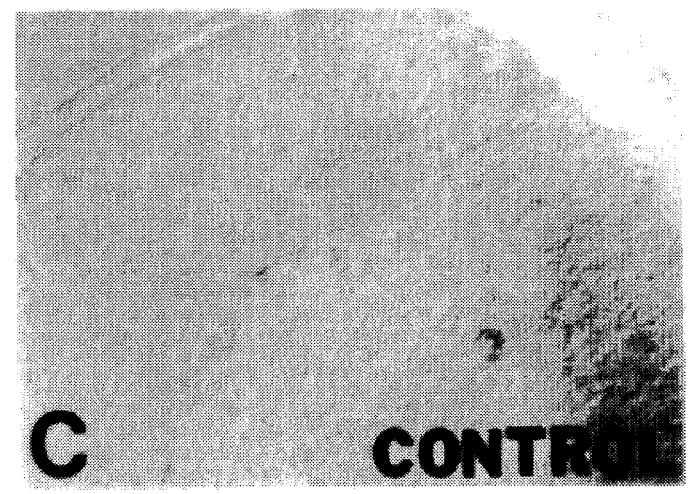

CAM-PDE has been previously localized by immunocytochemistry in the brain (Kincaid, et al. (1987) *Proc. Natl. Acad. USA*, 84:1118–1122). To ensure that our antibody selectively recognizes PDE, we conducted immunocytochemical examination in the cerebellum. As observed previously by Balaban, et al. (1989) *J. Neurosci.*, 9:2374–2381), CAM-PDE staining is highly localized to Purkinje cells and their processes (FIG. 8A). Calmodulin staining is also greatest in Purkinje cells, but also appears to a lesser extend in granule cells (FIG. 8B). Preabsorption with PDE eliminates staining by the CAM-PDE antibody (FIG. 8C).

We claim:

1. A method for enhancing the sense of smell in a human, said method consisting essentially of:

applying a phosphodiesterase inhibitor having inhibitory activity toward phosphodiesterase present in olfactory neurons to nasal epithelium in an amount sufficient to diminish the activity of said phosphodiesterase and enhance the sense of smell.

2. The method of claim 1 wherein the amount of inhibitor is sufficient to inhibit calcium/calmodulin activated phosphodiesterase.

3. The method of claim 1 wherein the inhibitor has at least ten-fold greater inhibitory activity toward calcium/calmodulin activated phosphodiesterase than toward calcium/calmodulin independent phosphodiesterases.

4. The method of claim 1 wherein the inhibitor is selected from the group consisting of caffeine, papaverine, theophylline, 2-O-propoxyphenyl-8-azapurin-6-one (M & B 22948), Vopocetine, TCV3-B and HA588.

5. The method of claim 3 wherein the inhibitor is a 7- or 8-alkyl isobutyl methyl xanthine.

6. The method of claim 3 wherein the inhibitor is 8-methoxy methyl isobutyl methyl xanthine.

7. The method of claim 3 wherein the inhibitor is methyl-3-isobutyl-8-methyl xanthine.

8. The method of claim 1 wherein the inhibitor is applied in the form of an aerosol.

9. The method of claim 3 wherein the inhibitor is volatile.

10. The method of claim 1 wherein the amount is sufficient to inhibit rolipram-inhibitable phosphodiesterase.

* * * * *